United States Patent
Nakajima et al.

(10) Patent No.: US 8,827,453 B2
(45) Date of Patent: Sep. 9, 2014

(54) OPHTHALMOLOGIC APPARATUS AND OPHTHALMOLOGIC OBSERVATION METHOD

(75) Inventors: Junko Nakajima, Tokyo (JP); Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 53 days.

(21) Appl. No.: 13/089,362

(22) Filed: Apr. 19, 2011

(65) Prior Publication Data

US 2011/0267581 A1  Nov. 3, 2011

(30) Foreign Application Priority Data

Apr. 30, 2010  (JP) ................................ 2010-105383

(51) Int. Cl.
    *A61B 3/14*  (2006.01)
    *A61B 3/10*  (2006.01)

(52) U.S. Cl.
    CPC ...................................... *A61B 3/102* (2013.01)
    USPC .......................................... 351/206; 351/205

(58) Field of Classification Search
    USPC ........................................................ 351/206
    See application file for complete search history.

(56) References Cited

U.S. PATENT DOCUMENTS

| | | | |
|---|---|---|---|
| 5,414,474 A | 5/1995 | Kamada et al. | |
| 5,598,248 A | 1/1997 | Nagano et al. | |
| 6,325,512 B1 | 12/2001 | Wei | |
| 6,714,669 B2 | 3/2004 | Some | |
| 7,506,978 B2 | 3/2009 | Nanjo | |
| 7,510,282 B2 | 3/2009 | Ueno et al. | |
| 7,639,845 B2 | 12/2009 | Utsunomiya | |
| 7,648,242 B2 | 1/2010 | Ferguson et al. | |
| 7,744,221 B2 | 6/2010 | Wei et al. | |
| 7,756,311 B2 | 7/2010 | Yasuno et al. | |
| 7,789,511 B2 | 9/2010 | Aoki et al. | |
| 7,809,166 B2 | 10/2010 | Funayama et al. | |
| 7,866,821 B2 | 1/2011 | Ferguson et al. | |

(Continued)

FOREIGN PATENT DOCUMENTS

| | | |
|---|---|---|
| EP | 1882445 A2 | 1/2008 |
| EP | 1894518 A1 | 3/2008 |

(Continued)

OTHER PUBLICATIONS

Communication dated Sep. 16, 2011, forwarding a European Search Report dated Sep. 8, 2011, in European Application No. 11163016.6-1265.

(Continued)

*Primary Examiner* — James Jones
(74) *Attorney, Agent, or Firm* — Fitzpatrick, Cella, Harper & Scinto (57) ABSTRACT

To accurately detect a movement of an object based on an image distorted by the movement of an eye to be inspected, which is acquired by a scanning imaging system, provided is an ophthalmologic apparatus including: an extraction means for extracting a plurality of characteristic images from a first fundus image of the eye to be inspected; a fundus image acquisition means for acquiring a second fundus image of the eye to be inspected during a period different from a period during which the first fundus image is acquired; and a calculation means for calculating at least a rotational movement of the eye to be inspected based on the plurality of characteristic images and the second fundus image.

33 Claims, 4 Drawing Sheets

(56) References Cited

U.S. PATENT DOCUMENTS

| | | |
|---|---|---|
| 2002/0003895 A1 | 1/2002 | Some |
| 2007/0052698 A1 | 3/2007 | Funayama et al. |
| 2007/0076217 A1 | 4/2007 | Baker et al. |
| 2007/0188707 A1 | 8/2007 | Nanjo |
| 2007/0195269 A1 | 8/2007 | Wei et al. |
| 2007/0263171 A1 | 11/2007 | Ferguson et al. |
| 2008/0009840 A1* | 1/2008 | Chernyak ............... 606/5 |
| 2008/0024721 A1 | 1/2008 | Ueno et al. |
| 2008/0259275 A1* | 10/2008 | Aoki et al. ............. 351/210 |
| 2010/0073634 A1 | 3/2010 | Ferguson et al. |
| 2010/0110171 A1 | 5/2010 | Satake |
| 2010/0142780 A1 | 6/2010 | Yasuno et al. |
| 2010/0182610 A1 | 7/2010 | Utsunomiya |
| 2010/0182612 A1 | 7/2010 | Yoshida et al. |
| 2011/0001930 A1 | 1/2011 | Levecq |
| 2011/0032479 A1 | 2/2011 | Utsunomiya |

FOREIGN PATENT DOCUMENTS

| | | | |
|---|---|---|---|
| JP | 4-236930 | A | 8/1992 |
| JP | 4-242630 | A | 8/1992 |
| JP | 5-250459 | A | 9/1993 |
| JP | 10-171995 | A | 6/1998 |
| JP | 11-253403 | A | 9/1999 |
| JP | 2001-283190 | A | 10/2001 |
| JP | 2004-512125 | A | 4/2004 |
| JP | 2006-235786 | A | 9/2006 |
| JP | 2007-130403 | A | 5/2007 |
| JP | 2007-202952 | A | 8/2007 |
| JP | 2008-029467 | A | 2/2008 |
| JP | 2008-054773 | A | 3/2008 |
| JP | 2008-210239 | A | 9/2008 |
| JP | 2008-310418 | A | 12/2008 |
| JP | 4222369 | B2 | 2/2009 |
| JP | 2009-523563 | A | 6/2009 |
| JP | 2009-535164 | A | 10/2009 |
| JP | 2010-110392 | A | 5/2010 |
| JP | 2011-135933 | A | 7/2011 |
| WO | 2008/113937 | A2 | 9/2008 |

OTHER PUBLICATIONS

Machine-produced English-language translation of JP 11-253403.
Machine-produced English-language translation of JP 2006-235786.
Machine-produced English-language translation of JP 11-253403. JP11253403 publication date Sep. 21, 1999.
Machine-produced English-language translation of JP 2006-235786. Publication date Sep. 7, 2006.

* cited by examiner

OPHTHALMOLOGIC APPARATUS AND OPHTHALMOLOGIC OBSERVATION METHOD

BACKGROUND OF THE INVENTION

1. Field of the Invention

The present invention relates to an ophthalmologic apparatus for acquiring a tomographic image of an eye to be inspected, and an ophthalmologic observation method of observing the eye to be inspected.

2. Description of the Related Art

At present, various different types of optical equipment are used as ophthalmic equipment. Of those, an eye can be observed with various types of equipment including an anterior ocular segment photographing device, a fundus camera, a confocal scanning laser ophthalmoscope (SLO), and an optical coherence tomography (OCT) apparatus that is an optical coherence tomographic imaging apparatus using optical interference of a low coherence light beam. In particular, optical tomographic imaging apparatuses are designed to obtain a high resolution tomographic image of a fundus, and are currently on the way to becoming an indispensable apparatus in outpatient clinics specialized in diagnosis of the retina. Hereinafter, optical tomographic imaging apparatuses including such OCT systems are referred as an OCT apparatuses.

In operation an OCT apparatus applies a low coherence light beam to a retina and measures reflected light from the sample (retina) with a high degree of sensitivity, by using an interferometer. Further, the OCT apparatus can obtain a tomographic image by scanning the low coherence light beam over the sample. In particular, the tomographic image of a retina is widely used in ophthalmic diagnosis.

In recent years, OCT apparatuses conventionally operated according to a, so-called, time domain method, in which a tomographic image is acquired by performing scanning along an optical path length of a reference beam in each tomographic acquisition position. However, OCT apparatuses have made a shift to a Fourier domain method of operation that eliminates the need for scanning along the optical path length of the reference beam in each tomographic acquisition position. Therefore, it is now possible, using the Fourier domain method, to acquire the tomographic image at a faster speed than before. The increase in the speed allows three-dimensional image taking of the fundus to be carried out, which has been difficult with the time domain method.

However, in three-dimensional imaging, two-dimensional scanning of the fundus is necessary even with the Fourier domain method, and hence the influence of an involuntary movement of an eye being scanned cannot be ignored. The influence of eye movements can be reduced by detecting the eye movements at the time of scanning and correcting a low coherence light beam scanned over the retina in synchronization with the detected eye movement. The eye movement can be detected by taking a fundus image of the eye in parallel with the image taking performed by the OCT apparatus and detecting displacements of characteristic points within the fundus image.

A system for acquiring the fundus image is divided into a one-time imaging system using the fundus camera and a scanning imaging system using the SLO. In general, when the scanning imaging system is used rather than the one-time imaging system, high contrast and high resolution may be realized. Therefore, in order to perform high-precision eye movement detection, the scanning imaging system is used. However, in the case of the scanning imaging system, a time lag occurs in a single acquired image. In other words, there is a time difference between the start and end of imaging. Thus, when the scanning imaging system is used to acquire an image of a fundus which is continuously moving, the acquired image distorts. In order to accurately detect the movement of the fundus, it is necessary to cancel the distortion in the single image.

Japanese Patent Application Laid-Open No. 2006-235786 discloses an invention for calculating the shift amounts of a plurality of images acquired by a scanning imaging system to perform position correction. In order to calculate the shift amounts, five parameters, that is, translation factors ($\Delta x, \Delta y$), a rotation factor ($\theta$), and magnification factors ($\beta x, \beta y$), are used.

However, the object of the invention disclosed in Japanese Patent Application Laid-Open No. 2006-235786 is to align images, each having a predetermined shift direction, into a single image, but does not describe any method for accurately detecting a movement of an object, for example, a complicated movement of an eye to be inspected.

SUMMARY OF THE INVENTION

The present invention has been made in view of the above-mentioned circumstances. An object of the present invention is to accurately detect a movement of an eye to be inspected based on an image distorted by the movement of the eye to be inspected, which is acquired by a scanning imaging system, to thereby obtain a suitable tomographic image.

In order to attain the above-mentioned object, an ophthalmologic apparatus according to the present invention includes: an extraction unit for extracting a plurality of characteristic images from a first fundus image of an eye to be inspected; a fundus image acquisition unit for acquiring a second fundus image of the eye to be inspected during a period different from a period during which the first fundus image is acquired; and a calculation unit for calculating at least a rotational movement of the eye to be inspected based on the plurality of characteristic images and the second fundus image.

Further, an ophthalmologic observation method according to the present invention includes: an extraction step of extracting a plurality of characteristic images from a first fundus image of an eye to be inspected; a fundus image acquisition step of acquiring a second fundus image of the eye to be inspected during a period different from a period during which the first fundus image is acquired; and a calculation step of calculating at least a rotational movement of the eye to be inspected based on the plurality of characteristic images and the second fundus image.

According to the present invention, the influence on rotation and magnification detection due to the distortion of an image of an object, which is caused by the movement of the object during the acquisition of a single image, may be cancelled based on temporally successive images obtained by the scanning imaging system, which enables accurate detection of the movement of the object. In other words, the position of the object moving at high speed in a complicated manner may be accurately detected unlike the conventional technologies.

Further features of the present invention will become apparent from the following description of embodiments with reference to the attached drawings.

DESCRIPTION OF THE EMBODIMENTS

An embodiment of the present invention is described in detail with reference to the attached drawings.

This embodiment describes a structure of an OCT apparatus for extracting templates (also referred to as "first characteristic points or first characteristic images") from a fundus image (also referred to as "first fundus image") (which is obtained by, for example, using a line-scan SLO), subjecting a newly (continuously) taken fundus image (also referred to as "second fundus image") to pattern matching (exploring the extracted characteristic images in the newly taken fundus image) to thereby detect an eye movement, and correcting a position of an OCT beam. A description is provided with reference to the optical structure diagram of FIG. 1, the block diagram of FIG. 2, the flowchart of FIG. 3, and the template diagram of FIG. 4. In this embodiment, a line scan SLO is used as a fundus movement detection apparatus. Any structure including a scanning imaging system, for example, a point scan SLO or an OCT apparatus using C-scan may be used.

Figure 1:
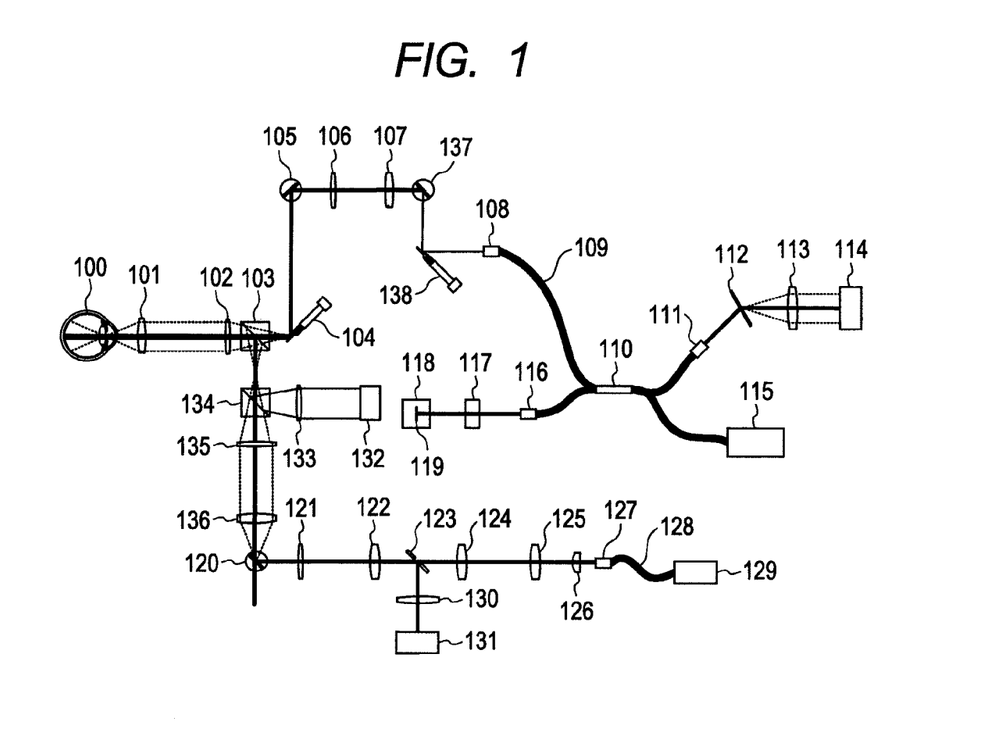
FIG. 1 is an optical structure diagram illustrating an OCT apparatus with a tracking function using a line scan SLO in an embodiment of the present invention.

FIG. 1 is the optical structure diagram of the OCT apparatus with a tracking function using a line-scan SLO. Of the OCT apparatus illustrated in FIG. 1, an SLO part is first described.

First, a beam emitted from a laser light source 129 passes through an optical fiber 128 and enters a fiber collimator 127 to become a collimated beam. The beam that has become the collimated beam enters a cylindrical lens 126 and spreads in a line shape. After that, the beam passes through relay lenses 124 and 125 and passes through a hole formed in a central part of a ring mirror 123. After that, the beam passes through relay lenses 121 and 122 and is deflected toward a predetermined direction by an SLO Y scanner 120. After that, the beam passes through relay lenses 135 and 136 and passes through a dichroic beam splitter 134 to travel toward a dichroic beam splitter 103. After that, the beam passes through relay lenses 101 and 102 to enter an eye 100 to be inspected and a linear beam is applied to the fundus of the eye 100 to be inspected. The Y scanner 120 is moved by a very small amount, and the fundus is scanned in a Y-direction with a linear beam extending in an X-direction.

The beam scattered at the fundus of the eye 100 to be inspected is collected for each line. That is, the beam scattered by the fundus exits from the eye 100 to be inspected, passes through the relay lenses 101 and 102, and is separated from a scattered OCT beam from the fundus, which is described later, by the dichroic beam splitter 103. After that, the beam is separated from a beam of a fixation index, which is described later, by the dichroic beam splitter 134, passes through the relay lenses 135 and 136, and hits the SLO Y scanner 120. After that, the beam passes through the relay lenses 121 and 122 and hits the ring mirror 123 being a mirror having a ring shape to be reflected. The beam reflected by the ring mirror 123 passes through a lens 130 and is detected by a line sensor 131.

Figure 2:
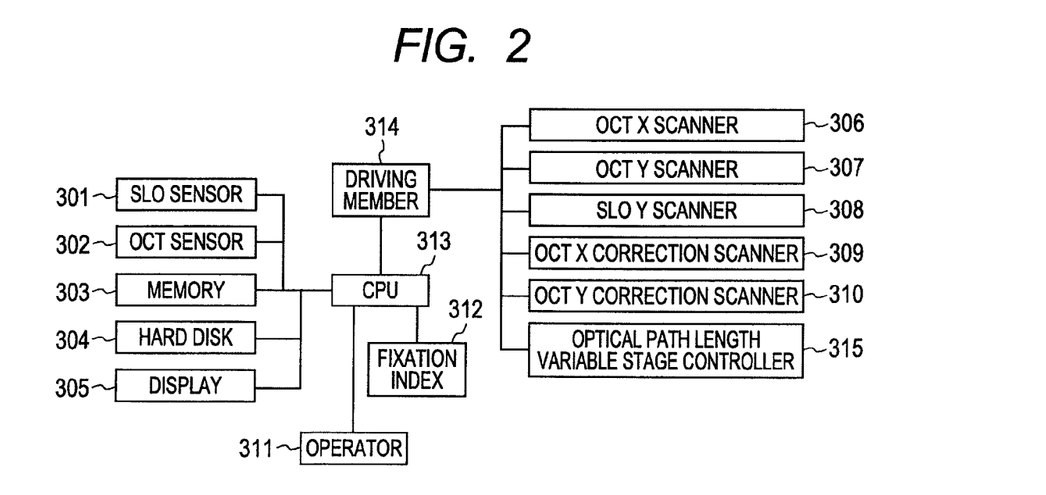
FIG. 2 is a block diagram illustrating a control part of the OCT apparatus with the tracking function using the line-scan SLO.

Intensity information on the beam detected by the line sensor 131 one line by one line is converted into a digital signal, sent to a CPU 313 of FIG. 2, processed by the CPU 313, and information on a plurality of lines of the beam are gathered to thereby become a two-dimensional fundus image. The two-dimensional fundus image is saved to a memory 303 or a hard disk 304 and displayed on a display 305 to allow an operator 311 to see the two-dimensional fundus image.

The structure for acquiring the SLO image corresponds to a fundus image acquisition unit in the present invention.

The SLO image acquired by the system described above is an image obtained by performing one-time imaging in the X-axis direction and scanning in the Y-direction, and hence the X-axis is referred to as a main scanning axis and the Y-axis is referred to as a sub scanning axis.

Next described is an OCT part of the OCT apparatus illustrated in FIG. 1. The beam emitted from a low coherence light source 115 passes through a fiber and enters a fiber coupler 110 to be branched into two beams in proportions according to the type of coupler. The two beams obtained after the branching are respectively referred to as a "reference beam" and a "sample beam". The reference beam passes through a fiber collimator 116 to exit to the outside, then passes through dispersion compensating glass 117, and is reflected by a reference mirror 119. The reference mirror 119 is fixed to an optical path length variable stage (OCT stage) 118 for changing an optical path length of the reference beam. The reflected reference beam follows the above-mentioned path in the reverse direction to return to the fiber coupler 110.

The sample beam passes through an optical fiber 109 and reaches a fiber collimator 108 to exit from the fiber collimator 108 to the outside. The sample beam hits an OCT X correction scanner 138 and then hits an OCT Y correction scanner 137 to be deflected toward a predetermined direction. After that, the sample beam passes through relay lenses 106 and 107 and hits an OCT Y scanner 105 and an OCT X scanner 104 to be deflected toward a predetermined direction. The reflected sample beam passes through the dichroic beam splitter 103 and an image plane thereof is adjusted by the scan lens 102. Then, the sample beam is stopped down by the eyepiece 101 to enter the eye 100 to be inspected and form an image on the fundus of the eye 100 to be inspected. The return beam from the fundus of the eye 100 to be inspected follows the above-mentioned path in the reverse direction to return to the fiber coupler 110.

The sample beam and the reference beam that have returned to the fiber coupler 110 are combined with each other at the fiber coupler 110 to cause interference. The interfered beam exits from a fiber collimator 111 to be dispersed by a transmission grating 112, passes through a lens 113, and is received by a line sensor 114. Intensity information on the beam received by the line sensor 114 is sent to the CPU 313 as a digital signal and subjected to a signal processing by the CPU 313 to become a two-dimensional tomographic image. A plurality of two-dimensional tomographic images thus obtained are saved to the memory 303 or the hard disk 304 of FIG. 2. Further, the two-dimensional tomographic images can be displayed on the display 305, which allows the operator 311 to see the two-dimensional tomographic images. The OCT part may be changed to the SLO part. The structure for acquiring the OCT images corresponds to a tomographic image acquisition unit in the present invention.

A fixation index 132 is located so as to be conjugated with the fundus. The beam emitted from the fixation index 132 passes through a lens 133 and the dichroic beam splitter 134 to travel toward the dichroic beam splitter 103. After that, the beam passes through the relay lenses 101 and 102 and forms an image on the fundus. It is possible to take two-dimensional images of the fundus in a desired position thereof by fixing a line of sight of the eye to be inspected to the fixation index, and the position for image taking is changed by changing a presentation position of the fixation index.

Next, a structure of a control part of the OCT apparatus according to this embodiment is described with reference to FIG. 2. FIG. 2 is a block diagram illustrating the control part of the OCT apparatus according to this embodiment.

The central processing unit (CPU) 313 is connected to the display 305, the hard disk 304, the memory 303, a fixation index 312, an OCT X correction scanner 309 (138), and an OCT Y correction scanner 310 (137). Further, the CPU 313 is connected to a scanner driving member 314 for driving the scanners and controls an OCT X scanner 306 (104), an OCT Y scanner 307 (105), and a SLO Y scanner 308 (120) through the scanner driving member 314. An OCT sensor 302 is connected as a sensor for the OCT part to the CPU 313. A SLO sensor 301 is connected as a sensor for the SLO part to the CPU 313.

Figure 3:
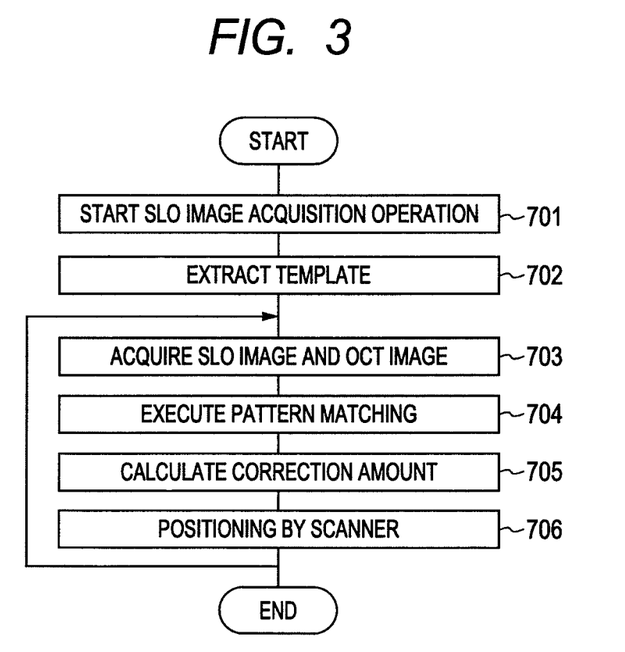
FIG. 3 is a flowchart illustrating an operation of the OCT apparatus with the tracking function using the line-scan SLO.

A method of analyzing the SLO image by the CPU 313 to obtain a correction amount and correcting a scanning position of the OCT beam in the system capable of simultaneously acquiring the SLO image and the OCT images is described with reference to a flowchart illustrated in FIG. 3.

The operator 311 roughly aligns the entire apparatus to the eye 100 to be inspected and adjusts the fixation index 312 (132). This way, the apparatus and the eye 100 to be inspected are adjusted in position to image a region to be imaged. When a signal indicating the completion of alignment (start of imaging) is input from an input section (not shown) by the operator 311, the CPU 313 proceeds to the start of SLO imaging of Step 701.

Figure 4:
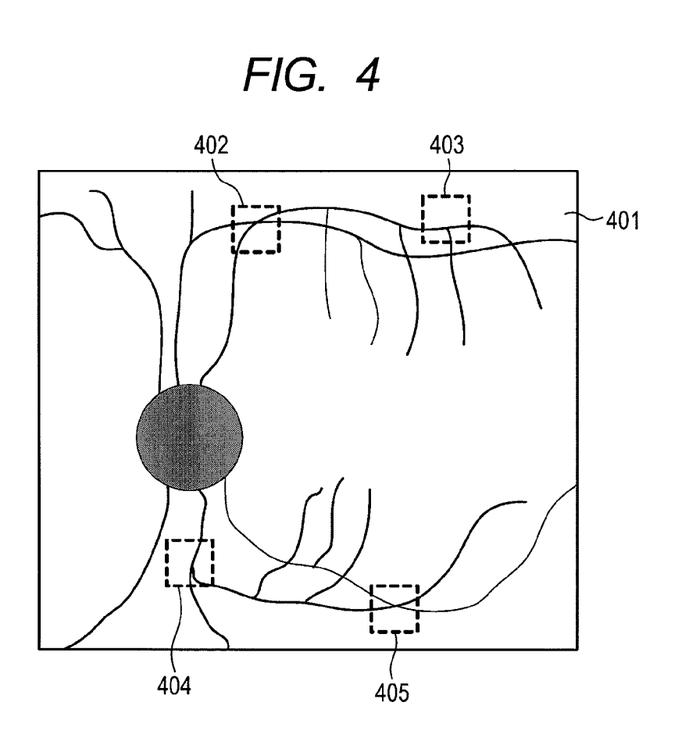
FIG. 4 illustrates template images.

After the SLO image, which is a first fundus image of the eye to be inspected, is acquired, the CPU 313 proceeds to Step 702 to extract, for example, at least three templates from an image 401 of the acquired SLO images illustrated in FIG. 4. The CPU 313 is configured to serve as an extraction unit for extracting a plurality of templates from the first fundus image of the eye to be inspected in the present invention. FIG. 4 is a concept diagram illustrating a relationship between the SLO image which is the fundus image and the templates. The templates correspond to small regions that have characteristics, that is, characteristic images, each of which has one of a line segment shape and an arbitrary two-dimensional pattern shape. In this embodiment, regions 402, 403, 404, and 405 illustrated in FIG. 4 are assumed as the templates. An extraction method to be used may be a known method and is not particularly limited. With respect to the extracted templates, images of the respective regions or characteristic amounts thereof, and coordinate positions of typical points on the extracted images are stored in the memory 303.

Hereinafter, the term "coordinates" refers to coordinates of the typical point on a small region. After the templates are determined, the CPU 313 proceeds to Step 703 to start the acquisition of the OCT images in parallel with the successive acquisition of the SLO image which is the second fundus image of the eye to be inspected during a period different from a period for acquiring the first fundus image.

An OCT imaging position may be specified by drawing a line on the SLO image displayed on the display 305 by the operator 311. Further, when a rectangle is drawn on the SLO image displayed on the display 305 by the operator 311 and a region specified by the rectangle is scanned with OCT, a three-dimensional retina image may be obtained. In any cases, regions which may be imaged by OCT are limited to regions located in the SLO image.

After the start of imaging with SLO and OCT, the CPU 313 proceeds to Step 704 to execute pattern matching on the successively acquired SLO images using the extracted templates 402, 403, 404, and 405. The pattern matching is processing for detecting locations most similar to the templates 402, 403, 404, and 405 from an image. In order to detect the most similar locations, for example, the following method is used. A part of the SLO image is cut into the same size as the template. A similarity between the cut part of the SLO image and the template is calculated. Assume that, when each of the cut part of the SLO image and the template has a size of n×m, a luminance value of the cut part of the SLO image is denoted by f[i,j] and a luminance value of the template image is denoted by t[i,j]. In order to calculate the similarity between the cut part of the SLO image and the template image, the following expression is used, $$\frac{\sum_{j=0}^{n-1}\sum_{i=0}^{m-1}(f[i,j]-\bar{f})(t[i,j]-\bar{t})}{\sqrt{\sum_{j=0}^{n-1}\sum_{i=0}^{m-1}(f[i,j]-\bar{f})^2}\sqrt{\sum_{j=0}^{n-1}\sum_{i=0}^{m-1}(t[i,j]-\bar{t})^2}} \quad \text{expression (1)}$$

where this calculation equation indicates the similarity, $\bar{f}$ and $\bar{t}$ indicate an averaging value of the luminance of the cut part of the SLO image and an averaging value of the luminance of the template, respectively. Next, a region of the SLO image which is obtained by shifting by one pixel in the X-axis direction from the cut position is cut into the same size as the template, and the similarity with the template is calculated in the same manner. Such an operation is repeated in both the X-axis direction and the Y-axis direction to calculate the similarity in all positions of the SLO image. A position in which the similarity is a maximum is assumed as the most similar location.

The CPU 313 executes the pattern matching to detect changes in positions of the templates 402, 403, 404, and 405. The CPU 313 is configured to serve as a unit for executing the pattern matching. The configuration corresponds to an exploration unit for exploring for the characteristic images corresponding to the templates previously extracted from the second fundus image.

Figure 5A:
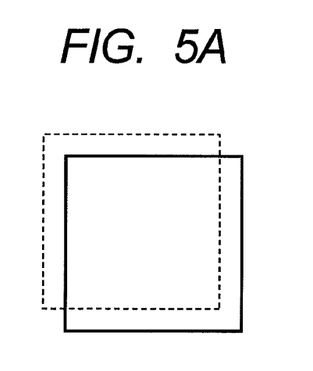
FIGS. 5A, 5B, and 5C illustrate three components of a movement of a fundus.
Figure 5B:
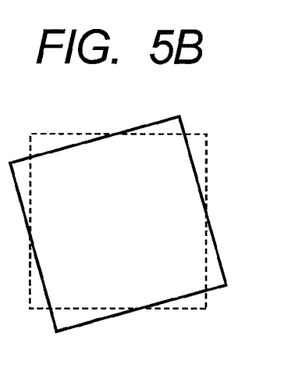
Figure 5C:
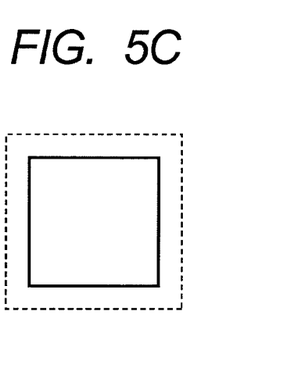

Next, the CPU 313 proceeds to Step 705 to analyze the movement of the fundus based on the changes in position information of the respective templates. The movement of the fundus may be divided into three kinds of components as illustrated in FIGS. 5A, 5B, and 5C. FIGS. 5A, 5B, and 5C are concept views illustrating the movement of the fundus, each of which shows that the positions of two SLO images are different from each other. Each of FIGS. 5A, 5B, and 5C illustrates a state of a compared image (image indicated by solid line) relative to a reference image (image indicated by broken line). The three kinds of components are a shift component illustrated in FIG. 5A, a rotation component illustrated in FIG. 5B, and a magnification change component illustrated in FIG. 5C. The shift component is a component in which the fundus is moved up and down and right and left. The rotation component is a component in which the eye rotates about the eye axis. The magnification change is a change in imaging magnification due to a change in distance from the apparatus when the eye moves in the eye axis direction. In other words, the change in imaging magnification is caused by a change in distance between the eyepiece and the fundus in the image optical axis on the imaging optical axis of the OCT apparatus. In order to detect the rotation component and the magnification change component, the at least three templates are extracted in Step 702. Affine transformation parameters are an X-axis direction shift component Sx, a Y-axis direction shift component Sy, a rotation angle θ, and a magnification β. The four parameters are obtained as follows.

First, the CPU 313 performs a calculation for separating the three kinds of components. The CPU 313 serves as a calculation unit for calculating at least the rotation component of the movement of the eye to be inspected in the present invention, and calculates at least the rotation component of the affine transformation parameters based on a result obtained by exploration by the exploration unit described above. The following affine transformation expression is used for separation. The affine transformation is a transformation including a translation (shift), a rotation, a change of magnification, and a shearing.

$$\begin{pmatrix} x' \\ y' \end{pmatrix} = \begin{pmatrix} a & b \\ c & d \end{pmatrix} \begin{pmatrix} x \\ y \end{pmatrix} + \begin{pmatrix} e \\ f \end{pmatrix} \quad \text{expression (2)}$$

where x and y respectively indicate an X-coordinate and a y-coordinate of one of the templates which are initially acquired, and x' and y' respectively indicate an X-coordinate and a y-coordinate in a position of another SLO image which is obtained by executing pattern matching on the another SLO image and corresponds to the one of the templates.

Parameters "a", "b", "c", "d", "e", and "f" are described with reference to FIGS. 6A to 6F. The images acquired by the system described above are described, and hence the X-axis corresponds to the main scanning axis and the Y-axis corresponds to the sub scanning axis.

Figure 6A:
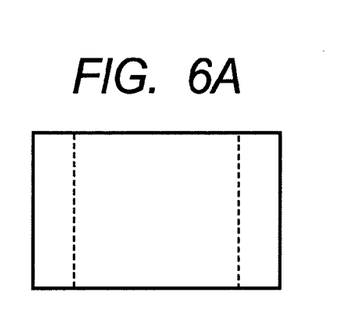
FIGS. 6A, 6B, 6C, 6D, 6E and 6F illustrate respective affine transformation parameters.
Figure 6B:
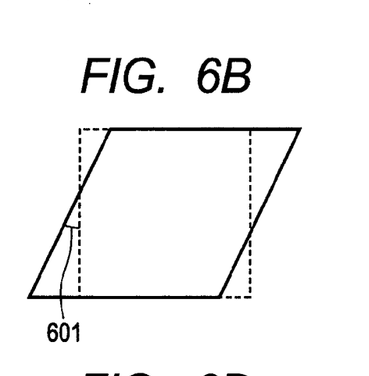
Figure 6C:
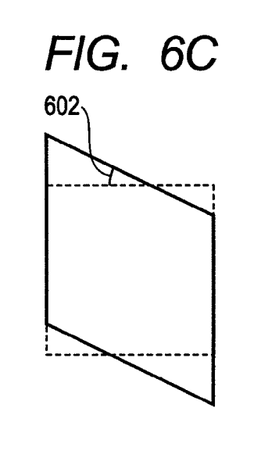
Figure 6D:
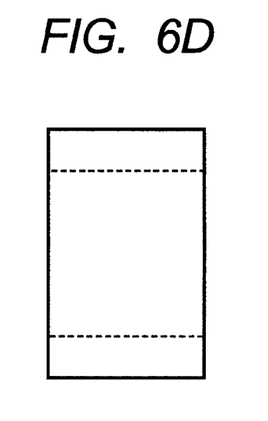
Figure 6E:
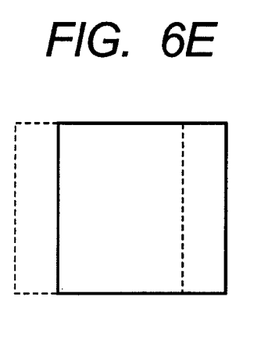
Figure 6F:
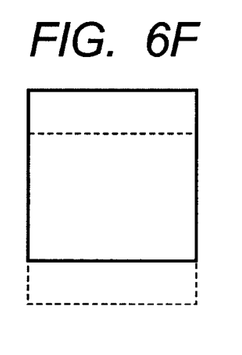

FIGS. 6A to 6F are concept diagrams illustrating the parameters "a", "b", "c", "d", "e", and "f", each of which illustrates two SLO images having different states. Each of FIGS. 6A to 6F illustrates a state of a compared image (image indicated by solid line) relative to a reference image (image indicated by broken line). The parameter "a" is a magnification component in the X-axis direction corresponding to the main scanning axis as illustrated in FIG. 6A. The parameter "d" is a magnification component in the Y-axis direction corresponding to the sub scanning axis as illustrated in FIG. 6D. The parameter "b" is a parallelogram distortion parallel to the X-axis as illustrated in FIG. 6B. The parameter "c" is a parallelogram distortion parallel to the Y-axis as illustrated in FIG. 6C. A value of the parameter "b" relates to an elevation or depression angle 601 relative to the Y-axis direction. A value of the parameter "c" relates to an elevation or depression angle 602 relative to the X-axis direction. The parameter "e" is a translation component in the X-axis direction as illustrated in FIG. 6E. The parameter "f" is a translation component in the Y-axis direction as illustrated in FIG. 6F. In order to obtain the six parameters, it is necessary to extract data in (x,y) coordinates obtained from at least three templates. The values of the parameters "a", "b", "c", "d", "e", and "f" satisfying Expression (2) in all the at least three templates are calculated by a least-squares method. In other words, with respect to the parameters "a", "b", and "e", when an error related to a template indicated by coordinates (x1,y1) of a typical point is denoted by δx1 and the following expression holds, $$ax_1 + by_1 + e - x'_1 = \delta x_1 \quad \text{expression (3)}$$

the parameters "a", "b", and "e" to minimize a sum of errors ($\Sigma(\delta x)^2$) related to all templates are calculated. The parameters "c", "d", and "f" are also calculated in the same manner.

Respective movements of the eyeball which correspond to the eye movement components indicated by the parameters "a", "b", "c", "d", "e", and "f" are described. The parameter "a" is the parameter exhibiting the change in magnification in the main scanning axis direction and thus exhibits the change in magnification due to the change in imaging magnification. The parameter "d" includes the change in magnification and the amount of movement of the fundus in the Y-axis direction during imaging. Therefore, the value of the parameter "a" is used as the pure change in magnification. The parameter "b" exhibits the amount of movement of the eyeball in the X-axis direction during sub scanning, but does not exhibit the rotation. The parameter "c" exhibits the pure rotation of the eyeball, and hence the value of the parameter "c" is used as the amount of rotation or rotation angle of the eyeball. The CPU 313 is configured to serve as a unit for obtaining the affine transformation parameters.

Of the obtained parameters, the parameters "a", "c", "e", and "f" are used to determine correction parameters. The X-axis direction shift component Sx, the Y-axis direction shift component Sy, the rotation angle indicated by θ, and the magnification indicated by β are corrected. In other words, correction expressions are as follows.

$$\begin{pmatrix} x' \\ y' \end{pmatrix} = \beta \begin{pmatrix} \cos\theta & -\sin\theta \\ \sin\theta & \cos\theta \end{pmatrix} \begin{pmatrix} x \\ y \end{pmatrix} + \begin{pmatrix} Sx \\ Sy \end{pmatrix} \quad \text{expression (4)}$$

From Expressions (2) and (4), the following expressions are obtained.

$$\beta = \sqrt{a^2 + c^2} \quad \text{expression (5)}$$

$$\theta = \arctan \frac{c}{a} \quad \text{expression (6)}$$

$$Sx = e \quad \text{expression (7)}$$

$$Sy = f \quad \text{expression (8)}$$

When all values of the parameters "a", "b", "c", "d", "e", and "f" are used as in a conventional example, the shift component is recognized as the rotation component or the magnification component during the acquisition of an image, and hence correction parameters different from correction parameters for an actual movement are calculated. However, when the parameters are used as described above, the correction values for the actual movement may be calculated.

A relation position change which is the amount of relative position change between an object and the imaging system is calculated from one of the object or the template image obtained from the object based on the correction values. The CPU 313 is configured to serve as a computing unit for computing the correction values and the relative position change.

After the calculation of the correction values is completed, the CPU 313 proceeds to Step 706 to send the obtained values to be corrected (β, θ, Sx, and Sy) to the OCT Y correction scanner 137 and the OCT X correction scanner 138, to thereby correct the scanning position of the OCT beam. The CPU 313 is configured to serve as a control unit for controlling operation units such as the OCT scanners based on the rotation of the movements of the eye to be inspected. The OCT Y correction scanner 137, the OCT X correction scanner 138, the scanner driving member 314, the OCT X scanner 104, and the OCT Y scanner 105 may share the correction of the beam scanning position. Alternately, the beam scanning position may be corrected only by the scanner driving member 314, the OCT X scanner 104, and the OCT Y scanner 105. As described above, the CPU 313 is configured to serve as a correction unit for correcting the beam scanning position based on the result obtained by the configuration serving as the computing unit described above. When the change in magnification in the main scanning direction is to be corrected, the CPU 313 serving as the control unit controls the optical path length variable stage 118 based on the calculated magnification to change the optical path length difference between the measuring beam and the reference beam.

The change in distance between the fundus of the eye 100 to be inspected and the eyepiece 101 may be obtained as the relative position change based on the correction value β. When the distance significantly changes, the fundus is located outside the OCT image, and hence the tomographic image of the fundus cannot be acquired. The change in distance between the fundus and the eyepiece which is obtained from the correction value β is corrected by moving the optical path length variable stage (OCT stage) 118. Therefore, the fundus may be prevented from being located outside the OCT image.

Thus, with the above-mentioned structure and configuration, an object movement detection apparatus capable of accurately determining the position of the object to be inspected that moves in a complicated manner, for example, the position of the eye, is obtained. Further, an OCT apparatus using the object movement detection apparatus capable of accurately determining the position of the object to be inspected to constantly acquire an image in an imaging location with high precision may be provided.

Another Embodiment

Further, the present invention is realized by executing the following processing. That is, in the processing, software (a program) for implementing the functions of the above-mentioned embodiment is supplied to a system or an apparatus via a network or various storage mediums and is read and executed by a computer (or CPU, MPU, or the like) of the system or the apparatus.

While the present invention has been described with reference to embodiments, it is to be understood that the invention is not limited to the disclosed embodiments.

This application claims the benefit of Japanese Patent Application No. 2010-105383, filed Apr. 30, 2010, which is hereby incorporated by reference herein in its entirety.

What is claimed is:

1. An ophthalmologic apparatus, comprising:
a fundus image acquisition unit arranged to acquire a first fundus image of an eye to be inspected and a second fundus image of the eye during a period different from a period during which the first fundus image is acquired;
an extraction unit arranged to extract a plurality of characteristic images from the first fundus image of the eye to be inspected; and
a calculation unit arranged to calculate at least a rotational movement of the eye to be inspected based on the plurality of characteristic images and the second fundus image.

2. An ophthalmologic apparatus according to claim 1, wherein the fundus image acquisition unit is arranged to acquire the first fundus image and the second fundus image based on a return beam from the eye to be inspected irradiated with a measuring beam via a scanning unit, and
wherein the ophthalmologic apparatus further comprises a control unit arranged to control the scanning unit based on the calculated rotational movement of the eye to be inspected.

3. An ophthalmologic apparatus according to claim 1, further comprising:
a tomographic image acquisition unit arranged to acquire a tomographic image of the eye to be inspected based on a combined beam obtained by combining (a) a return beam from the eye to be inspected, irradiated with a measuring beam via a scanning unit, and (b) a reference beam corresponding to the measuring beam; and
a control unit arranged to control the scanning unit based on the calculated rotational movement of the eye to be inspected.

4. An ophthalmologic apparatus according to claim 3, wherein the calculation unit is arranged to calculate at least a magnification of an image of the eye to be inspected, and
wherein the control unit arranged to change an optical path length difference between the measuring beam and the reference beam based on the calculated magnification.

5. An ophthalmologic apparatus according to claim 1, wherein the plurality of characteristic images comprise at least three characteristic images,
wherein the ophthalmologic apparatus further comprises an exploration unit arranged to explore characteristic images corresponding to the at least three characteristic images in the second fundus image, and
wherein the calculation unit is arranged to calculate at least a rotation parameter of affine transformation parameters based on an exploration result obtained by the exploration unit.

6. An ophthalmologic method, comprising:
a fundus image acquisition step of acquiring a first fundus image of an eye to be inspected and a second fundus image of the eye during a period different from a period during which the first fundus image is acquired;
an extraction step of extracting a plurality of characteristic images from said first fundus image of the eye to be inspected; and
a calculation step of calculating at least a rotational movement of the eye to be inspected based on the plurality of characteristic images and the second fundus image.

7. An ophthalmologic method according to claim 6, wherein the fundus image acquisition step comprises acquiring the first fundus image and the second fundus image based on a return beam from the eye to be inspected irradiated with a measuring beam via a scanning unit, and
wherein the ophthalmologic method further comprises a control step of controlling the scanning unit based on the calculated rotational movement of the eye to be inspected.

8. An ophthalmologic method according to claim 6, further comprising:
a tomographic image acquisition step of acquiring a tomographic image of the eye to be inspected based on a combined beam obtained by combining (a) a return beam from the eye to be inspected, irradiated with a measuring beam via a scanning unit, and (b) a reference beam corresponding to the measuring beam; and
a control step of controlling the scanning unit based on the calculated rotational movement of the eye to be inspected.

9. An ophthalmologic method according to claim 8, wherein the calculation step comprises calculating at least a magnification of an image of the eye to be inspected, and
    wherein the control step comprises changing an optical path length difference between the measuring beam and the reference beam based on the calculated magnification.

10. An ophthalmologic method according to claim 6, wherein the plurality of characteristic images comprise at least three characteristic images;
    wherein the ophthalmologic observation method further comprises an exploration step of exploring characteristic images corresponding to the at least three characteristic images in the second fundus image, and
    wherein the calculation step comprises calculating at least a rotation parameter of affine transformation parameters based on an exploration result obtained in the exploration step.

11. An ophthalmologic apparatus, comprising:
    an extraction unit configured to extract a plurality of characteristic images from a first fundus image of an eye to be inspected;
    a fundus image acquisition unit configured to acquire a second fundus image of the eye to be inspected during a period different from a period during which the first fundus image is acquired;
    a calculation unit configured to calculate at least a magnification of an image of the eye to be inspected based on the plurality of characteristic images and the second fundus image; and
    a control unit configured to change an optical path length difference between a measuring beam emitted to the eye to be inspected and a reference beam corresponding to the measuring beam based on the calculated magnification.

12. An ophthalmologic apparatus according to claim 11, further comprising a tomographic image acquisition unit configured to acquire a tomographic image of the eye to be inspected based on a combined beam obtained by combining (a) a return beam from the eye to be inspected irradiated with the measuring beam via a scanning unit, and (b) the reference beam,
    wherein the control unit controls the scanning unit based on the calculated rotational movement of the eye to be inspected.

13. An ophthalmologic apparatus according to claim 11, wherein the fundus image acquisition unit acquires the first fundus image and the second fundus image based on a return beam from the eye to be inspected irradiated with the measuring beam via a scanning unit, and
    wherein the control unit controls the scanning unit based on the calculated rotational movement of the eye to be inspected.

14. An ophthalmologic apparatus according to claim 11, wherein the plurality of characteristic images comprise at least three characteristic images,
    wherein the ophthalmologic apparatus further comprises an exploration unit configured to explore characteristic images corresponding to the at least three characteristic images in the second fundus image, and
    wherein the calculation unit calculates at least a magnification parameter of affine transformation parameters based on an exploration result obtained by the exploration unit.

15. A method comprising:
    an extraction step of extracting a plurality of characteristic images from a first fundus image of an eye to be inspected;
    a fundus image acquisition step of acquiring a second fundus image of the eye to be inspected during a period different from a period during which the first fundus image is acquired;
    a calculation step of calculating at least a magnification of an image of the eye to be inspected based on the plurality of characteristic images and the second fundus image; and
    a control step of changing an optical path length difference between a measuring beam emitted to the eye to be inspected and a reference beam corresponding to the measuring beam based on the calculated magnification.

16. A method according to claim 15, further comprising a tomographic image acquisition step of acquiring a tomographic image of the eye to be inspected based on a combined beam obtained by combining (a) a return beam from the eye to be inspected, irradiated with the measuring beam via a scanning unit, and (b) the reference beam,
    wherein the control step controls the scanning unit based on the calculated rotational movement of the eye to be inspected.

17. A method according to claim 15, wherein the fundus image acquisition step acquires the first fundus image and the second fundus image based on a return beam from the eye to be inspected, irradiated with the measuring beam via a scanning unit, and
    wherein the control step controls the scanning unit based on the calculated rotational movement of the eye to be inspected.

18. A method according to claim 15, wherein the plurality of characteristic images comprise at least three characteristic images,
    wherein the method further comprises an exploration step of exploring characteristic images corresponding to the at least three characteristic images in the second fundus image, and
    wherein the calculation step calculates at least a magnification parameter of affine transformation parameters based on an exploration result obtained by the exploration step.

19. A non-transitory apparatus-readable storage medium storing a program that causes an apparatus to effect the method according to claim 6.

20. A non-transitory apparatus-readable storage medium storing a program that causes an apparatus to effect the method according to claim 15.

21. An ophthalmologic apparatus according to claim 1, further comprising:
    a tomographic image acquisition unit arranged to acquire a tomographic image of the eye to be inspected based on a combined beam obtained by combining (a) a return beam from the eye to be inspected, on which a measuring beam is emitted, and (b) a reference beam corresponding to the measuring beam; and
    a correction unit arranged to correct an acquisition position of the tomographic image based on the calculated rotational movement.

22. An ophthalmologic method according to claim 6, further comprising:
    a tomographic image acquisition step of acquiring a tomographic image of the eye to be inspected based on a combined beam obtained by combining (a) a return beam from the eye to be inspected, on which a measuring beam is emitted, and (b) a reference beam corresponding to the measuring beam; and a correction step of correcting an acquisition position of the tomographic image based on the calculated rotational movement.

23. An ophthalmologic apparatus according to claim 1, wherein the fundus image acquisition unit includes an imaging system which comprises (a) an imaging unit which temporally images successive images of the fundus of the eye to be inspected to image the first fundus image and the second fundus image, and (b) a light receiving unit which receives a combined beam generated by combining (1) a return beam from the eye to be inspected on which a measuring beam is emitted, and (2) a reference beam corresponding to the measuring beam to image a tomographic image of the eye to be inspected.

24. An ophthalmologic method according to claim 6, wherein the fundus image acquisition step includes a step of imaging the fundus image by using an imaging system which comprises (a) an imaging unit which temporally images successive images of the fundus of the eye to be inspected to image the first fundus image and the second fundus image, and (b) a light receiving unit which receives a combined beam generated by combining (1) a return beam from the eye to be inspected on which a measuring beam is emitted, and (2) a reference beam corresponding to the measuring beam to image a tomographic image of the eye to be inspected.

25. An ophthalmologic apparatus according to claim 11, wherein the fundus image acquisition unit includes an imaging system which comprises (a) an imaging unit which temporally images successive images of the fundus of the eye to be inspected to images the plurality of fundus images, and (b) a light receiving unit which receives a combined beam generated by combining (1) a return beam from the eye to be inspected on which a measuring beam is emitted, and (2) a reference beam corresponding to the measuring beam to image a tomographic image of the eye to be inspected.

26. A method according to claim 15, wherein the fundus image acquisition step includes a step of imaging the fundus image by using an imaging system which comprises (a) an imaging unit which temporally images successive images of the fundus of the eye to be inspected to image the plurality of fundus images, and (b) a light receiving unit which receives a combined beam generated by combining (1) a return beam from the eye to be inspected on which a measuring beam is emitted, and (2) a reference beam corresponding to the measuring beam to image a tomographic image of the eye to be inspected.

27. An ophthalmologic apparatus according to claim 1, wherein the calculation unit is arranged to calculate at least an amount and a direction of the rotational movement based on the plurality of characteristic images and the second fundus image.

28. An ophthalmologic method according to claim 6, wherein the calculating step comprises a step of calculating at least an amount and a direction of the rotational movement based on the plurality of characteristic images and the second fundus image.

29. An ophthalmologic apparatus according to claim 11, wherein the calculation unit is arranged to calculate at least an amount and a direction of the rotational movement based on the plurality of characteristic images and the second fundus image.

30. A method according to claim 15, wherein the calculation step comprises a step of calculating at least an amount and a direction of the rotational movement based on the plurality of characteristic images and the second fundus image.

31. An ophthalmologic apparatus comprising:
an imaging system including an imaging unit for imaging a fundus image of an eye to be inspected;
a unit arranged to execute a matching operation by using a plurality of characteristic areas within each of a plurality of fundus images imaged by the imaging unit;
a unit arranged to obtain a parameter for an affine transformation based on a result of the matching operation; and
a unit arranged to obtain a relative positional movement of the eye to be inspected with respect to the imaging unit in a direction of an optical axis of the imaging unit, by using a parameter designating a variation of a size of the plurality of fundus images among the parameters of the affine transformation.

32. An ophthalmologic method comprising:
an imaging step of imaging a fundus image of the eye to be inspected by an imaging system including an imaging unit;
a step of executing a matching operation by using a plurality of characteristic areas within each of a plurality of fundus images imaged by the imaging unit;
a step of obtaining a parameter for an affine transformation based on a result of the matching operation; and
a step of obtaining a relative positional movement of the eye to be inspected with respect to the imaging unit in a direction of an optical axis of the imaging unit, by using a parameter designating a variation of a size of the plurality of fundus images among the parameters of the affine transformation.

33. A non-transitory apparatus-readable storage medium storing a program that causes an apparatus to effect the method according to claim 32.

* * * * *